(12) United States Patent
Hoss et al.

(10) Patent No.: US 7,826,879 B2
(45) Date of Patent: *Nov. 2, 2010

(54) ANALYTE SENSORS AND METHODS OF USE

(75) Inventors: Udo Hoss, Alameda, CA (US); Zenghe Liu, Alameda, CA (US); Benjamin J. Feldman, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 974 days.

This patent is subject to a terminal disclaimer.

(21) Appl. No.: 11/365,169

(22) Filed: Feb. 28, 2006

(65) Prior Publication Data

US 2007/0203407 A1    Aug. 30, 2007

(51) Int. Cl.
*A61B 5/05* (2006.01)
*A61B 5/1473* (2006.01)

(52) U.S. Cl. .................. 600/347; 600/345; 600/365; 204/403.01; 204/403.14

(58) Field of Classification Search ......... 600/300–301, 600/306–309, 345–365, 372, 385–390, 346; 604/174–180; 128/897–898, 903, 904, 920; 204/403, 406, 408, 412, 403.01, 403.14; 205/779
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,425,920 A | 1/1984 | Bourland et al. | |

(Continued)

FOREIGN PATENT DOCUMENTS

EP    0 320 109 A1    6/1989

(Continued)

OTHER PUBLICATIONS

International Search Report and Written Opinion of the International Searching Authority for International Application No. PCT/US2007/062915 filed Feb. 27, 2007 to Abbott Diabetes Care, Inc.

(Continued)

*Primary Examiner*—Alexa D Neckel
*Assistant Examiner*—Jennifer Dieterle
(74) *Attorney, Agent, or Firm*—Jackson & Co., LLP

(57) ABSTRACT

An analyte sensor system including a substrate, a first electrode disposed on a first surface of the substrate, a second electrode disposed on a second surface of the substrate, a third electrode provided in electrical contact with at least one of the first or second electrodes, where at least a portion of the first electrode and the second electrode are subcutaneously positioned in a patient, and where the third electrode is substantially entirely positioned external to the patient, and corresponding methods are provided.

24 Claims, 3 Drawing Sheets

U.S. PATENT DOCUMENTS

| | | | |
|---|---|---|---|
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,703,756 A | 11/1987 | Gough et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,854,322 A | 8/1989 | Ash et al. | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,082,550 A | 1/1992 | Rishpon et al. | |
| 5,106,365 A | 4/1992 | Hernandez | |
| 5,122,925 A | 6/1992 | Inpyn | |
| 5,165,407 A | 11/1992 | Wilson et al. | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A * | 1/1997 | Heller et al. | 435/14 |
| 5,601,435 A | 2/1997 | Quy | |
| 5,609,575 A | 3/1997 | Larson et al. | |
| 5,628,310 A | 5/1997 | Rao et al. | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,735,285 A | 4/1998 | Albert et al. | |
| 5,772,586 A | 6/1998 | Heinonen et al. | |
| 5,791,344 A | 8/1998 | Schulman et al. | |
| 5,899,855 A | 5/1999 | Brown | |
| 5,925,021 A | 7/1999 | Castellano et al. | |
| 5,942,979 A | 8/1999 | Luppino | |
| 5,957,854 A | 9/1999 | Besson et al. | |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,024,699 A | 2/2000 | Surwit et al. | |
| 6,049,727 A | 4/2000 | Crothall | |
| 6,083,710 A | 7/2000 | Heller et al. | |
| 6,088,608 A | 7/2000 | Schulman et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,159,147 A | 12/2000 | Lichter et al. | |
| 6,162,611 A | 12/2000 | Heller et al. | |
| 6,175,752 B1 * | 1/2001 | Say et al. | 600/345 |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,275,717 B1 | 8/2001 | Gross et al. | |
| 6,283,761 B1 | 9/2001 | Joao | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,348,640 B1 | 2/2002 | Navot et al. | |
| 6,359,444 B1 | 3/2002 | Grimes | |
| 6,360,888 B1 | 3/2002 | McIvor et al. | |
| 6,366,794 B1 | 4/2002 | Moussy et al. | |
| 6,377,828 B1 | 4/2002 | Chaiken et al. | |
| 6,379,301 B1 | 4/2002 | Worthington et al. | |
| 6,418,346 B1 | 7/2002 | Nelson et al. | |
| 6,424,847 B1 | 7/2002 | Mastrototaro et al. | |
| 6,427,088 B1 | 7/2002 | Bowman, IV et al. | |
| 6,440,068 B1 | 8/2002 | Brown et al. | |
| 6,478,736 B1 | 11/2002 | Mault | |
| 6,484,046 B1 | 11/2002 | Say et al. | |
| 6,497,655 B1 | 12/2002 | Linberg et al. | |
| 6,514,689 B2 | 2/2003 | Han et al. | |
| 6,514,718 B2 | 2/2003 | Heller et al. | |
| 6,522,927 B1 | 2/2003 | Bishay et al. | |
| 6,549,796 B2 | 4/2003 | Sohrab | |
| 6,551,494 B1 | 4/2003 | Heller et al. | |
| 6,558,320 B1 | 5/2003 | Causey, III et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,591,125 B1 | 7/2003 | Buse et al. | |

| | | |
|---|---|---|
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,125,382 B2 | 10/2006 | Zhou et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,225,535 B2 | 6/2007 | Feldman et al. |
| 7,226,978 B2 | 6/2007 | Tapsak et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,291,497 B2 | 11/2007 | Holmes et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,386,937 B2 | 6/2008 | Bhullar et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,565,197 B2 | 7/2009 | Haubrich et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2002/0019022 A1 | 2/2002 | Dunn et al. |
| 2002/0042090 A1 | 4/2002 | Heller et al. |
| 2002/0050250 A1 * | 5/2002 | Peterson et al. ............. 119/721 |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0152622 A1 | 8/2004 | Keith et al. |
| 2004/0167801 A1 | 8/2004 | Say et al. |
| 2004/0171921 A1 | 9/2004 | Say et al. |

| | | | | | | |
|---|---|---|---|---|---|---|
| 2004/0176672 A1 | 9/2004 | Silver et al. | | 2007/0078322 A1 | 4/2007 | Stafford |
| 2004/0186362 A1 | 9/2004 | Brauker et al. | | 2007/0106135 A1 | 5/2007 | Sloan et al. |
| 2004/0186365 A1 | 9/2004 | Jin et al. | | 2007/0149875 A1 | 6/2007 | Ouyang et al. |
| 2004/0193090 A1 | 9/2004 | Lebel et al. | | 2007/0156033 A1 | 7/2007 | Causey, III et al. |
| 2004/0199059 A1 | 10/2004 | Brauker et al. | | 2007/0163880 A1 | 7/2007 | Woo et al. |
| 2004/0204687 A1 | 10/2004 | Mogensen et al. | | 2007/0173706 A1 | 7/2007 | Neinast et al. |
| 2004/0225338 A1 | 11/2004 | Lebel et al. | | 2007/0191701 A1 | 8/2007 | Feldman et al. |
| 2004/0236200 A1 | 11/2004 | Say et al. | | 2007/0203407 A1 | 8/2007 | Hoss et al. |
| 2004/0254433 A1 | 12/2004 | Bandis et al. | | 2007/0203966 A1 | 8/2007 | Brauker et al. |
| 2004/0254434 A1 | 12/2004 | Goodnow et al. | | 2007/0235331 A1 | 10/2007 | Simpson et al. |
| 2004/0267300 A1 | 12/2004 | Mace | | 2007/0244383 A1 | 10/2007 | Talbot et al. |
| 2005/0003470 A1 | 1/2005 | Nelson et al. | | 2007/0249922 A1 | 10/2007 | Peyser et al. |
| 2005/0004494 A1 | 1/2005 | Perez et al. | | 2007/0255531 A1 | 11/2007 | Drew |
| 2005/0010269 A1 | 1/2005 | Lebel et al. | | 2007/0258395 A1 | 11/2007 | Jollota et al. |
| 2005/0027177 A1 | 2/2005 | Shin et al. | | 2008/0009692 A1 | 1/2008 | Stafford |
| 2005/0031689 A1 | 2/2005 | Shults et al. | | 2008/0017522 A1 | 1/2008 | Heller et al. |
| 2005/0043598 A1 | 2/2005 | Goode, Jr. et al. | | 2008/0021666 A1 | 1/2008 | Goode, Jr. et al. |
| 2005/0090607 A1 | 4/2005 | Tapsak et al. | | 2008/0029391 A1 | 2/2008 | Mao et al. |
| 2005/0103624 A1 | 5/2005 | Bhullar et al. | | 2008/0030369 A1 | 2/2008 | Mann et al. |
| 2005/0112169 A1 | 5/2005 | Brauker et al. | | 2008/0033254 A1 | 2/2008 | Kamath et al. |
| 2005/0114068 A1 | 5/2005 | Chey et al. | | 2008/0039702 A1 | 2/2008 | Hayter et al. |
| 2005/0121322 A1 | 6/2005 | Say et al. | | 2008/0045824 A1 | 2/2008 | Tapsak et al. |
| 2005/0131346 A1 | 6/2005 | Douglas | | 2008/0064943 A1 | 3/2008 | Talbot et al. |
| 2005/0143635 A1 | 6/2005 | Kamath et al. | | 2008/0071156 A1 | 3/2008 | Brister et al. |
| 2005/0176136 A1 | 8/2005 | Burd et al. | | 2008/0071328 A1 | 3/2008 | Haubrich et al. |
| 2005/0182306 A1 | 8/2005 | Sloan | | 2008/0083617 A1 | 4/2008 | Simpson et al. |
| 2005/0187720 A1 | 8/2005 | Goode, Jr. et al. | | 2008/0086042 A1 | 4/2008 | Brister et al. |
| 2005/0192557 A1 | 9/2005 | Brauker et al. | | 2008/0086044 A1 | 4/2008 | Brister et al. |
| 2005/0195930 A1 | 9/2005 | Spital et al. | | 2008/0086273 A1 | 4/2008 | Shults et al. |
| 2005/0199494 A1 | 9/2005 | Say et al. | | 2008/0108942 A1 | 5/2008 | Brister et al. |
| 2005/0203360 A1 | 9/2005 | Brauker et al. | | 2008/0119705 A1 | 5/2008 | Patel et al. |
| 2005/0239154 A1 | 10/2005 | Feldman et al. | | 2008/0183061 A1 | 7/2008 | Goode, Jr. et al. |
| 2005/0239156 A1 | 10/2005 | Drucker et al. | | 2008/0183399 A1 | 7/2008 | Goode, Jr. et al. |
| 2005/0241957 A1 | 11/2005 | Mao et al. | | 2008/0188731 A1 | 8/2008 | Brister et al. |
| 2005/0245795 A1 | 11/2005 | Goode, Jr. et al. | | 2008/0189051 A1 | 8/2008 | Goode, Jr. et al. |
| 2005/0245799 A1 | 11/2005 | Brauker et al. | | 2008/0194935 A1 | 8/2008 | Brister et al. |
| 2005/0277164 A1 | 12/2005 | Drucker et al. | | 2008/0194936 A1 | 8/2008 | Goode, Jr. et al. |
| 2005/0287620 A1 | 12/2005 | Heller et al. | | 2008/0194937 A1 | 8/2008 | Goode, Jr. et al. |
| 2006/0001538 A1 | 1/2006 | Kraft et al. | | 2008/0194938 A1 | 8/2008 | Brister et al. |
| 2006/0010098 A1 | 1/2006 | Goodnow et al. | | 2008/0195232 A1 | 8/2008 | Carr-Brendel et al. |
| 2006/0015020 A1 | 1/2006 | Neale et al. | | 2008/0195967 A1 | 8/2008 | Goode, Jr. et al. |
| 2006/0015024 A1 | 1/2006 | Brister et al. | | 2008/0197024 A1 | 8/2008 | Simpson et al. |
| 2006/0016700 A1 | 1/2006 | Brister et al. | | 2008/0200788 A1 | 8/2008 | Brister et al. |
| 2006/0019327 A1 | 1/2006 | Brister et al. | | 2008/0200789 A1 | 8/2008 | Brister et al. |
| 2006/0020186 A1 | 1/2006 | Brister et al. | | 2008/0200791 A1 | 8/2008 | Simpson et al. |
| 2006/0020187 A1 | 1/2006 | Brister et al. | | 2008/0208025 A1 | 8/2008 | Shults et al. |
| 2006/0020188 A1 | 1/2006 | Kamath et al. | | 2008/0214915 A1 | 9/2008 | Brister et al. |
| 2006/0020189 A1 | 1/2006 | Brister et al. | | 2008/0214918 A1 | 9/2008 | Brister et al. |
| 2006/0020190 A1 | 1/2006 | Kamath et al. | | 2008/0228051 A1 | 9/2008 | Shults et al. |
| 2006/0020191 A1 | 1/2006 | Brister et al. | | 2008/0228054 A1 | 9/2008 | Shults et al. |
| 2006/0020192 A1 | 1/2006 | Brister et al. | | 2008/0235469 A1 | 9/2008 | Drew |
| 2006/0036139 A1 | 2/2006 | Brister et al. | | 2008/0242961 A1 | 10/2008 | Brister et al. |
| 2006/0036140 A1 | 2/2006 | Brister et al. | | 2008/0255438 A1 | 10/2008 | Saidara et al. |
| 2006/0036141 A1 | 2/2006 | Kamath et al. | | 2008/0262469 A1 | 10/2008 | Brister et al. |
| 2006/0036142 A1 | 2/2006 | Brister et al. | | 2008/0275313 A1 | 11/2008 | Brister et al. |
| 2006/0036143 A1 | 2/2006 | Brister et al. | | 2008/0287764 A1 | 11/2008 | Rasdal et al. |
| 2006/0036144 A1 | 2/2006 | Brister et al. | | 2008/0287765 A1 | 11/2008 | Rasdal et al. |
| 2006/0036145 A1 | 2/2006 | Brister et al. | | 2008/0287766 A1 | 11/2008 | Rasdal et al. |
| 2006/0166629 A1 | 7/2006 | Reggiardo | | 2008/0296155 A1 | 12/2008 | Shults et al. |
| 2006/0173444 A1 | 8/2006 | Choy et al. | | 2008/0306368 A1 | 12/2008 | Goode, Jr. et al. |
| 2006/0189863 A1 | 8/2006 | Peyser et al. | | 2008/0306434 A1 | 12/2008 | Dobbles et al. |
| 2006/0222566 A1 | 10/2006 | Brauker et al. | | 2008/0306435 A1 | 12/2008 | Kamath et al. |
| 2006/0226985 A1 | 10/2006 | Goodnow et al. | | 2008/0306444 A1 | 12/2008 | Brister et al. |
| 2006/0247508 A1 | 11/2006 | Fennell | | 2008/0312518 A1 | 12/2008 | Jina et al. |
| 2006/0247710 A1 | 11/2006 | Goetz et al. | | 2009/0005666 A1 | 1/2009 | Shin et al. |
| 2006/0253085 A1 | 11/2006 | Geismar et al. | | 2009/0012379 A1 | 1/2009 | Goode, Jr. et al. |
| 2006/0253086 A1 | 11/2006 | Moberg et al. | | 2009/0018424 A1 | 1/2009 | Kamath et al. |
| 2006/0287691 A1 | 12/2006 | Drew | | 2009/0018425 A1 | 1/2009 | Ouyang et al. |
| 2007/0027381 A1 | 2/2007 | Stafford | | 2009/0020502 A1 | 1/2009 | Bhullar et al. |
| 2007/0060814 A1 | 3/2007 | Stafford | | 2009/0030294 A1 | 1/2009 | Petisce et al. |
| 2007/0073129 A1 | 3/2007 | Shah et al. | | 2009/0036758 A1 | 2/2009 | Brauker et al. |
| 2007/0078320 A1 | 4/2007 | Stafford | | 2009/0036763 A1 | 2/2009 | Brauker et al. |
| 2007/0078321 A1 | 4/2007 | Mazza et al. | | 2009/0043181 A1 | 2/2009 | Brauker et al. |

| | | |
|---|---|---|
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0099436 A1 | 4/2009 | Brister et al. |
| 2009/0112478 A1 | 4/2009 | Mueller, Jr. et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| WO | WO 2004/061420 A2 | 7/2004 |
| WO | WO 2004/061420 A3 | 7/2004 |
| WO | WO 2005/089103 A2 | 9/2005 |
| WO | WO 2005/089103 A3 | 9/2005 |
| WO | WO 2006/079114 A2 | 7/2006 |
| WO | WO 2006/118947 A2 | 11/2006 |

OTHER PUBLICATIONS

International Preliminary Report on Patentability and Written Opinion of the International Searching Authority for PCT Application No. PCT/US2007/062915 filed Feb. 27, 2007 to Abbott Diabetes Care, Inc., mailed Sep. 12, 2008.

U.S. Appl. No. 12/533,742, Office Action mailed Jan. 11, 2010.

* cited by examiner

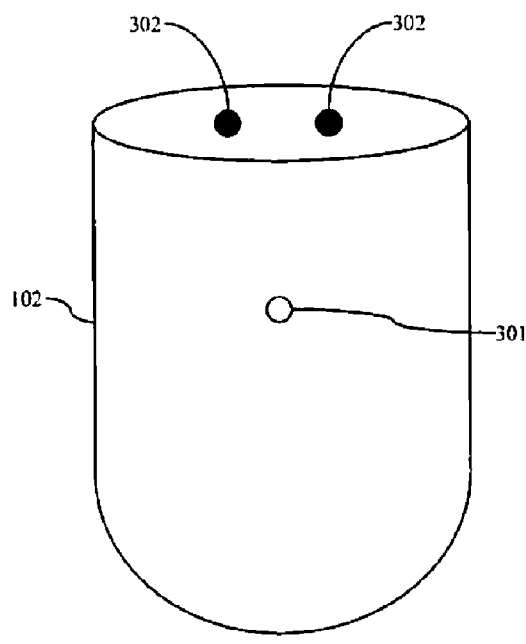
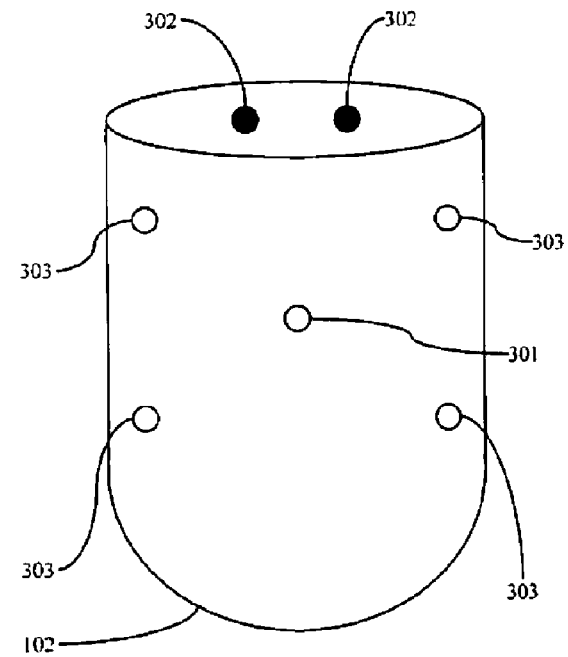
FIGURE 3A
FIGURE 3B
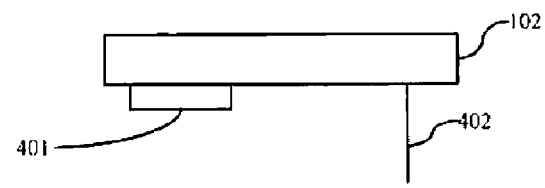
FIGURE 4A
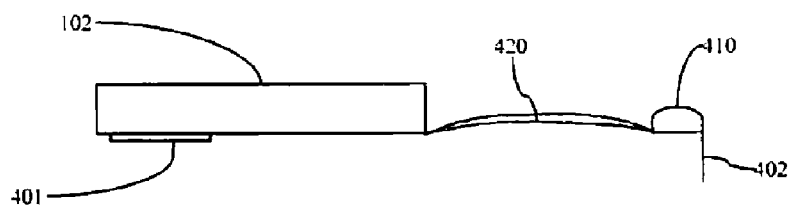
FIGURE 4B
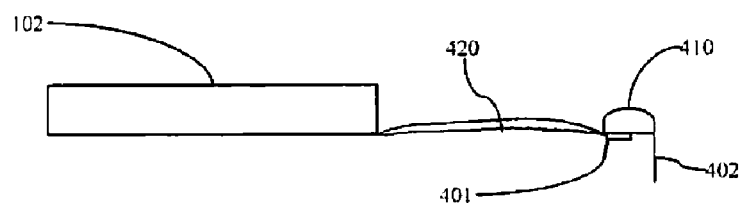
FIGURE 4C

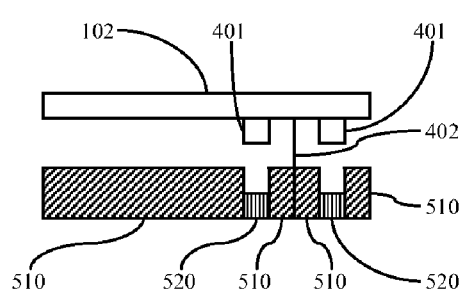
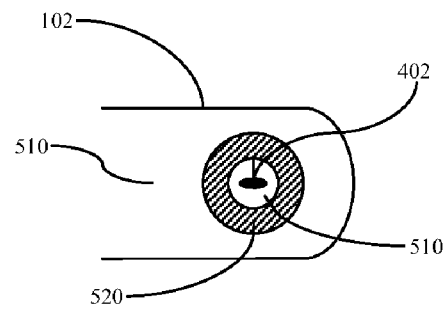
FIGURE 5A                           FIGURE 5B
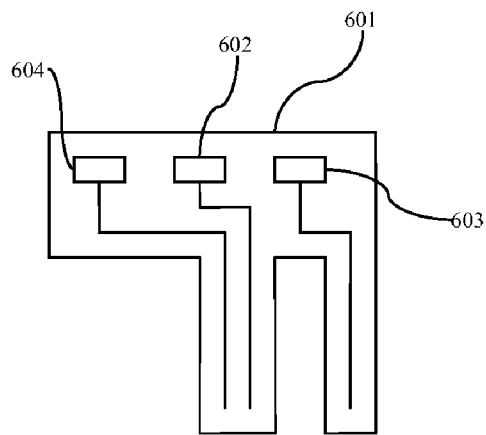
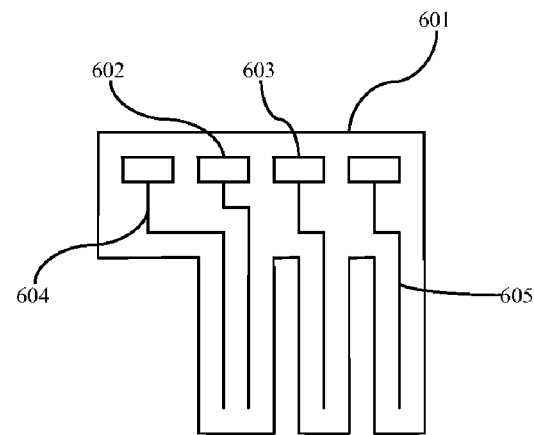
FIGURE 6A                           FIGURE 6B
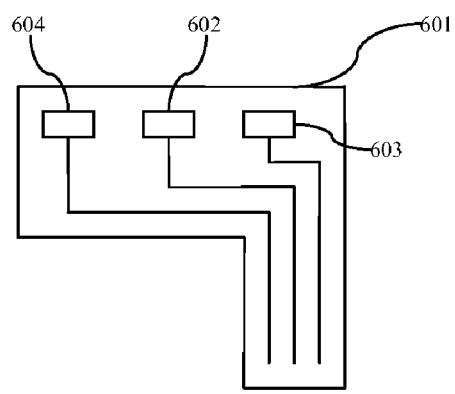
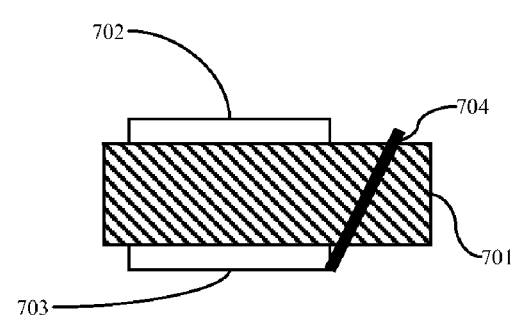
FIGURE 6C                           FIGURE 7

ANALYTE SENSORS AND METHODS OF USE

BACKGROUND

Continuous analyte monitoring systems such as continuous glucose monitoring systems use analyte sensors a portion of which is placed in contact with the patient's bodily fluid such as interstitial fluid or blood. The analyte sensor such as glucose sensors are configured with electrodes such as a working electrode, a counter electrode and a reference electrode, and where at least a portion of the sensor is placed in vivo so as to detect the level of the patient's analyte. In the three electrode configuration, the reference electrode is maintained substantially current free, and is configured to establish a substantially constant electrical potential difference with respect to the working electrode. The electrical potential difference then is used to drive certain electrochemical reactions that result in a current signal which is directly proportional to the level of analyte in the patient (such as the patient's glucose concentration).

The analyte sensor configuration described above, and in most glucose sensors that employ multiple electrodes for detecting the glucose level, for example, the counter electrode is generally configured to close the circuit. That is, since the electrons resulting from the electrochemical reactions by the analyte sensor are flowing into the working electrode from the electrolyte solution (the patient's body), the counter electrode of the analyte sensor needs to dispose of the electrons back into the electrolyte (that is, the counter electrode must find molecules or ions that can be reduced). The applied electrical potential at the counter electrode is regulated through a feedback loop such that the necessary reduction reactions can take place. Therefore, it is necessary for the counter electrode of the analyte sensor be electrically coupled to the human body.

In view of the foregoing, it would be desirable to have methods and device for providing a compact, cost effective analyte sensor configuration. Indeed, it would be desirable to have methods and device for providing analyte sensors with external counter electrode which is not placed in vivo along with the working and reference electrodes of the analyte sensor so as to be in fluid contact with the patient's analyte. Moreover, it would be desirable to have method and system for manufacturing analyte sensors to achieve cost effectiveness and scalability by, for example, reducing the number of necessary manufacturing steps.

SUMMARY OF THE INVENTION

In view of the foregoing, in accordance with the various embodiments of the present invention, there is provided methods and devices for analyte sensor configuration with an external on-body counter electrode forming a two electrode analyte sensor such as glucose sensors, which is provided with the working and reference electrodes at least a portion of each of which are placed in fluid contact with the patient's analyte, and which is provided with an external non-invasive counter electrode provided on the patient's skin.

These and other objects, features and advantages of the present invention will become more fully apparent from the following detailed description of the embodiments, the appended claims and the accompanying drawings.

BRIEF DESCRIPTION OF THE DRAWINGS

FIGS. 3A-3B illustrate a bottom view of the transmitter unit housing with counter electrode contact in accordance with one embodiment of the present invention;

FIGS. 4A-4C each illustrates the transmitter unit coupled with an analyte sensor with external counter electrode in accordance with various alternate embodiments of the present invention;

FIGS. 5A and 5B illustrate the side cross-sectional view and bottom view of the transmitter unit coupled with an analyte sensor with external counter electrode with dislocation detection mechanism in accordance with one embodiment of the present invention;

FIG. 6A illustrates a two working electrode analyte sensor with external counter electrode, FIG. 6B illustrates a three working electrode analyte sensor with external counter electrode in accordance with various embodiments of the present invention, and FIG. 6C illustrates a two working electrode analyte sensor with external counter electrode of another embodiment; and FIG. 7 illustrates a cross sectional view of a two sided analyte sensor with external counter electrode in accordance with one embodiment of the present invention.

DETAILED DESCRIPTION

Figure 1:
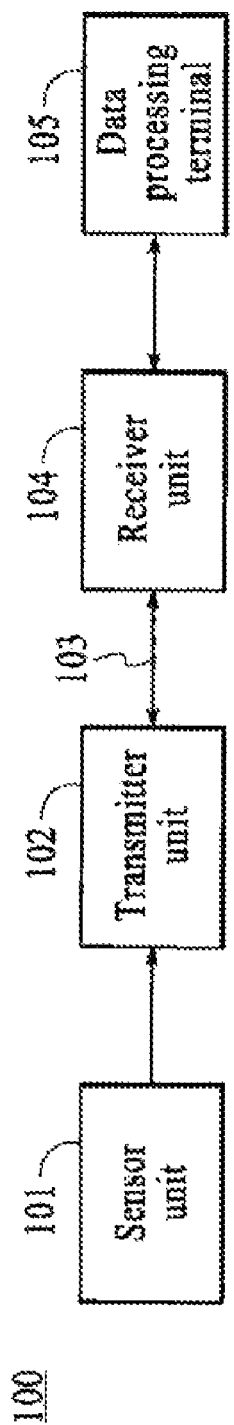
FIG. 1 illustrates a data monitoring and management system such as, for example, an analyte monitoring system 100 for practicing one embodiment of the present invention.

FIG. 1 illustrates a data monitoring and management system such as, for example, an analyte monitoring system 100 for practicing one embodiment of the present invention. In such embodiment, the analyte monitoring system 100 includes an analyte sensor 101, a transmitter unit 102 coupled to the sensor 101, and a receiver unit 104 which is configured to communicate with the transmitter unit 102 via a communication link 103. The receiver unit 104 may be further configured to transmit data to a data processing terminal 105 for evaluating the data received by the receiver unit 104.

Only one sensor 101, transmitter unit 102, communication link 103, receiver unit 104, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, receiver unit 104, and data processing terminal 105, where each receiver unit 104 is uniquely synchronized with a respective transmitter unit 102. Moreover, within the scope of the present invention, the analyte monitoring system 100 may be a continuous monitoring system, or a semi-continuous or discrete monitoring system.

In one embodiment of the present invention, the sensor 101 is physically positioned on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled glucose level of the user, for transmission to the receiver unit 104 via the communication link 103.

Additional analytes that may be monitored or determined by sensor 101 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

In one embodiment, the analyte monitoring system 100 is configured as a one-way RF communication path from the transmitter unit 102 to the receiver unit 104. In such embodiment, the transmitter unit 102 transmits the sampled data signals received from the sensor 101 without acknowledgement from the receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the receiver unit 104 may be configured to detect such transmitted encoded sampled data signals at predetermined time intervals. Alternatively, the analyte monitoring system 10 may be configured with a bi-directional RF communication between the transmitter unit 102 and the receiver unit 104.

Additionally, in one aspect, the receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the receiver unit 104 is a data processing section which is configured to process the data signals received from the transmitter unit 102 such as by performing data decoding, error detection and correction, data clock generation, and data bit recovery.

In operation, upon completing the power-on procedure, the receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the receiver unit 104 is configured to begin receiving from the transmitter unit 102 data signals corresponding to the user's detected analyte level. More specifically, the receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump, which may be configured to administer insulin to patients, and which is configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses (e.g., correction bolus, carbohydrate bolus, dual wave bolus including normal and extended bolus such as square wave bolus, and so on) for administration based on, among others, the detected analyte levels received from the transmitter unit 102.

Figure 2:
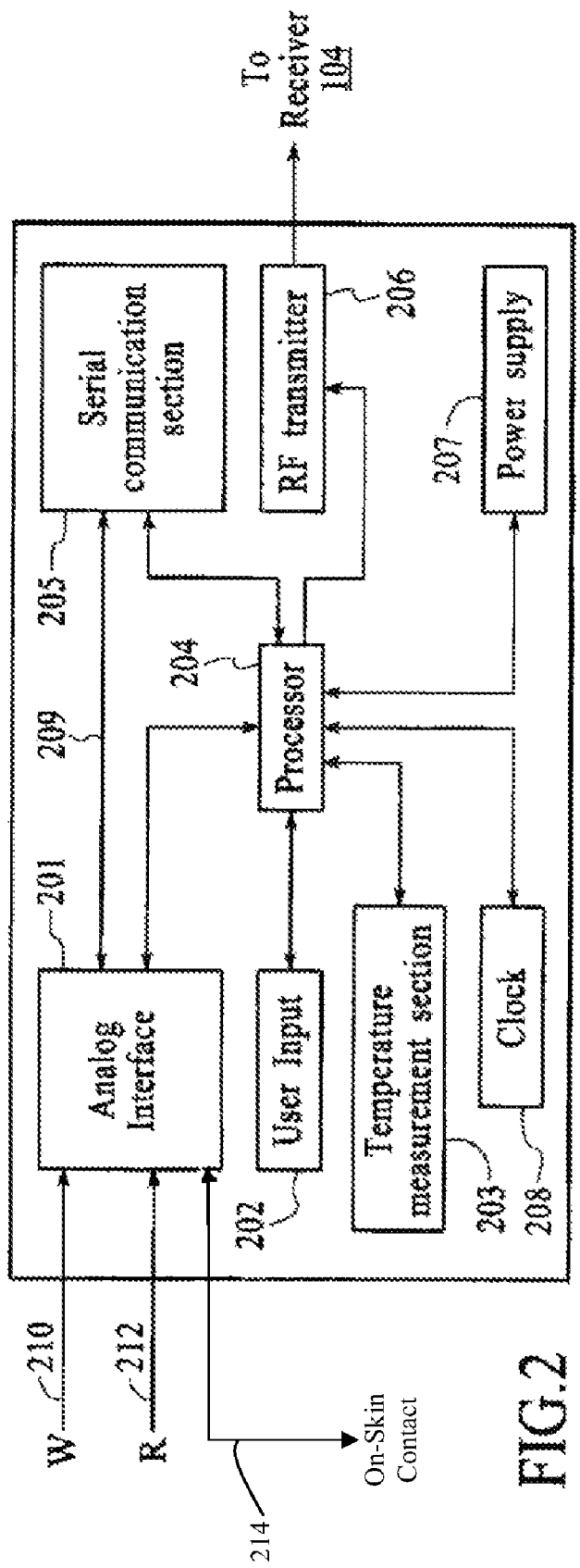
FIG. 2 is a block diagram of the transmitter unit of the data monitoring and detection system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided two contacts working electrode (W) 210 and reference electrode (R) 212, each operatively coupled to the analog interface 201 of the transmitter unit 102 for connection to the sensor unit 201 (FIG. 1). In one embodiment, the working electrode (W) 210 and reference electrode (R) 212 may be made using a conductive material that is either printed or etched, for example, such as carbon which may be printed, or metal foil (e.g., gold) which may be etched.

Referring to FIG. 2, also shown I the transmitter unit 102 is a contact 214 which is operatively coupled to the analog interface 201. In one embodiment, the contact 214 is configured to function as the external counter electrode and is positioned so as to establish physical contact with the skin surface of the patient wearing the transmitter unit on body.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the receiver 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the receiver 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the receiver 104 under the control of the transmitter processor 204. Furthermore, the power supply 207 may include a commercially available battery.

The transmitter unit 102 is also configured such that the power supply section 207 is capable of providing power to the transmitter for a minimum of three months of continuous operation after having been stored for 18 months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the receiver 104.

Additional detailed description of the analyte monitoring system, its various components including the functional descriptions of the transmitter unit are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

FIGS. 3A-3B illustrate a bottom view of the transmitter unit housing with counter electrode contact in accordance with one embodiment of the present invention. Referring to FIG. 3A, the housing of the transmitter unit 102 is provided with a temperature probe 301 on the bottom surface of the transmitter unit 102 housing. In one embodiment, the temperature probe 301 is operatively coupled to the temperature measurement section 203 (FIG. 2) of the transmitter unit 102, and configured to monitor the temperature of the skin near the sensor insertion site. The temperature reading is used to adjust or modify the analyte readings obtained from the analog interface 201. Also shown in FIG. 3A is a plurality of contact points 302, two of which are configured to operatively couple to a respective one of the working electrode and the reference electrode of the analyte sensor.

In this manner, in one embodiment of the present invention, using the two electrode analyte sensor, the counter reference point is provided by the skin contact point established with a connection to the conductive exterior housing of the temperature probe 301. Accordingly, the analyte sensor may be configured with working electrode and the reference electrode only, and the counter electrode may be provided external to the patient's body.

Referring now to FIG. 3B, there is provided a plurality of contacts 303 disposed substantially at a predetermined pattern (for example, concentric, circular, or any other suitable spatial arrangement or distribution) on the bottom surface of the transmitter unit 102. Each of the plurality of contacts 303 are configured to establish on-skin contact when the transmitter unit 102 is worn on the patient's body. Moreover, each of the plurality of contacts 303 is configured for electrical communication with the counter electrode connection 214 (FIG. 2).

Moreover, in one embodiment, by providing a plurality of counter electrode contacts on the external surface of the transmitter unit 102 housing in contact with the patient's skin, slight displacement of the transmitter unit 102 and/or the sensor segment (including the working and the reference electrodes in fluid contact with the patient's analytes) ensures that the external counter electrode 214 connection to the transmitter unit 102 is retained even if one or more of the counter electrode contact 603 temporarily separate from physically connecting to the patient's skin. In this manner, an effective redundancy is provided to improve potential sensor failure modes by having a separate connection to the external counter electrode 214.

FIGS. 4A-4C each illustrates the transmitter unit coupled with an analyte sensor with external counter electrode in accordance with various alternate embodiments of the present invention. Referring to FIG. 4A, transmitter unit 102 is operatively coupled to an analyte sensor system which includes a first sensor segment 402 including the working and reference electrodes, and at least a portion of which is configured to be placed subcutaneously in a patient, so as to maintain fluid contact with the patient's analyte. Additionally, there is also provided a second sensor segment 401 including a counter electrode which is provided wholly and substantially entirely outside of the patient's body, and in electrical contact with the transmitter unit 102. More specifically, in one embodiment, the second sensor segment 401 including the counter electrode is provided on the transmitter unit 102 so as to be in physical contact with the patient's skin during the time that the transmitter unit 102 is worn by the patient (e.g., by placement and securement of the transmitter unit 102 on the patient's skin).

Referring to FIG. 4B, it can be seen that the transmitter unit 102 is coupled to a sensor housing 410 by a physical connection 420 which may include, among others, a cable connection. In this embodiment, the first sensor segment 402 is provided in the sensor housing 410 as shown in the Figure, while the second sensor segment 401 is provided on the transmitter unit 102 housing. The sensor housing 410 in one embodiment is configured to be positioned on the patient's skin, and further, to retain the subcutaneously placed first sensor segment 402 in fluid contact with the patient's analyte. In one embodiment, the physical connection 420 is configured to provide electrical connection between the transmitter unit 102 and the first sensor segment 402 such that the detected analyte level of the patient from the first sensor segment 402 may be provided to the transmitter unit 102 for data transmission and/or processing.

Referring to FIG. 4C, it can be seen that the first sensor segment 402 including the working electrode and the reference electrode, and the second sensor segment 401 including the counter electrode of the analyte sensor, are both provided in the sensor housing 410. More specifically, compared to the embodiment shown in FIG. 4B, the first sensor segment 401 as shown in FIG. 4C is provided on the sensor housing 410 so as to be in physical contact with the surface of the patient's skin. In this manner, the first sensor segment 420 and the second sensor segment 410 are both configured for electrical communication with the transmitter unit 102 by the physical connection 420.

FIGS. 5A and 5B illustrate the side cross-sectional view and bottom view of the transmitter unit coupled with an analyte sensor with external counter electrode with dislocation detection mechanism in accordance with one embodiment of the present invention. It can be seen that the illustration shown in FIG. 5B is along the direction following arrow A shown in FIG. 5A. Referring to FIGS. 5A and 5B, there is provided an insulation layer 510 which is provided between the patient's skin and the transmitter unit 102. For example, the insulation layer 510 may include an adhesive layer for securely retaining the transmitter unit 102 on the patient's skin. Also shown in FIGS. 5A-5B is a conductive segment 520 disposed in the insulation layer 510 to substantially surround the first sensor segment 402, and which is configured to physically couple with the second sensor segment 401 including the counter electrode of the sensor 101.

In this manner, in one embodiment of the present invention, the counter electrode of the second sensor segment 401 maintains contact with the patient's skin through the conductive segment 520 of the insulation layer 510, and when the transmitter unit 102 is dislocated (for example, by inadvertent movement of the transmitter unit 102 housing after placement on the patient, and thus dislocating the position of the sensor 101), interruption of the contact between the first sensor segment 402 and the conductive segment 520 of the insulation layer 510 may be detected through a change in the counter electrode voltage level. This change in voltage level at the counter electrode may be associated with an alarm condition on the transmitter unit 102 detected by the processor unit 204 (FIG. 2), to provide a warning to the patient indicating a dislocation of the transmitter unit 102, and further, a possible sensor dislocation from the measuring site of the patient that may lead to erroneous and/or no measured data associated with the patient's analyte level.

FIG. 6A illustrates a two working electrode analyte sensor with external counter electrode, FIG. 6B illustrates a three working electrode analyte sensor with external counter electrode in accordance with various embodiments of the present invention, and FIG. 6C illustrates a two working electrode analyte sensor with external counter electrode of another embodiment. Referring to FIG. 6A, a sensor system in one embodiment may include a substrate layer 601 with two working electrodes 602, 603 disposed thereon, as well as a reference electrode 604. Since the counter electrode in the three electrode sensor system in one embodiment is provided externally, using substantially the same sensor dimensions, a two working electrode sensor system may be obtained. Furthermore, since the counter electrode of the second sensor segment 401 is placed external to the patient, in one embodiment, the plurality of working electrodes 602, 603 may share the same external counter electrode of the second sensor segment 401.

Referring to FIG. 6B, in yet another embodiment, a third working electrode 605 may be configured to be part of the sensor system that includes a counter electrode (external), a reference electrode 604, and multiple working electrodes 602, 603, 605. In this manner, multiple working electrodes in the analyte sensor system may improve and/or facilitate sensor calibration and accuracy of measured data. In addition, each of the three working electrodes 602, 603, 605 (or more), may be configured to work with a single external counter electrode of the second sensor segment 401. Referring now to FIG. 6C, a sensor electrode configuration in accordance with still another embodiment includes two working electrodes 602, 603 and a reference electrode 604 provided on the substrate 601, where the three electrodes are configured to be in electrical communication with the single external counter electrode (FIG. 2, contact 214, for example). Compared with the embodiment shown in FIG. 6A, the analyte sensor system shown in FIG. 6C is provided with a one segment of the sensor which is configured to be in fluid contact with the analyte of the patient (rather than two segments, one for each working electrode as shown in FIG. 6A).

FIG. 7 illustrates a cross sectional view of a two sided analyte sensor with external counter electrode in accordance with one embodiment of the present invention. Referring to FIG. 7, a two sided three electrode sensor system is provided with a substrate 701 with a working electrode 702 disposed on a first side of the substrate 701, and a reference electrode 703 disposed on a second side of the substrate 701, the first and second sides of the substrate 701 being opposite sides. As compared with a single sided sensor configuration where each electrode layer separated by a thin layer of insulation material such as Melinex, in the embodiment shown in FIG. 7, the working electrode 701 is separated from the reference electrode 702 by the relatively thick substrate layer 701.

In this manner, during the screen printing process for manufacturing the sensors, the potential for the thin insulation layer shorting the two electrode layers that it is separating can be minimized since the thickness of the substrate layer 701 provides substantial separation between the working electrode layer 702 and the reference electrode layer 703. Moreover, referring back to FIG. 7, in one embodiment, there is provided a conducting path such as a via 704 through the substrate layer 701 so as to provide the sensor electrode contacts on the same side of the substrate 701. The via 704 in one embodiment is configured to provide electrical connection between the reference electrode 703 and the opposite side of the substrate layer 701 so that the transmitter unit 102 may be electrically coupled to the sensor on the side of the sensor where the working electrode 702 is disposed. Moreover, in the case where the transmitter contacts are disposed on the reference electrode 703 side of the sensor, the via 704 may be positioned on the reference electrode layer 703.

Alternatively, the via 704 may be removed from the sensor configuration in which case, the transmitter unit 102 is configured to electrically coupled to the sensor on both sides of the substrate 701 to establish electrical connection to the working electrode 702 and the reference electrode 703. For example, referring back to FIGS. 4B and 4C, it can be seen that the sensor housing 410 may include contacts for each of the working, reference and counter electrodes so as to electrically communicate with the transmitter unit 102 over the connection 420. In this case, the sensor housing 410 may be configured to provide electrical contacts to both sides of the sensor substrate 701 so that the sensor housing 420 may be configured to establish electrical contacts with the working electrode 702 and the reference electrode 703 disposed on opposite sides of the substrate layer 701.

In the manner described above, in accordance with the various embodiments of the present invention, it is possible to achieve cost reduction and/or increased yield in the manufacturing of analyte sensors by, for example, removing the counter electrode from the sensor configuration which, in the screen printing process or any other processes for manufacturing the analyte sensors for example, may eliminate a number of necessary and/or critical manufacturing steps. For example, in one embodiment, it may no longer be necessary to obtain precise alignment of the carbon layers for the electrodes during the screen printing process in the manufacturing of the two sided analyte sensor, as there is no potential for shorting the electrodes through the thin insulation layers disposed between the carbon layers during the manufacturing process. Moreover, in one embodiment, by providing the working and the reference electrodes on two opposite surfaces of the analyte sensor, it may be possible to achieve cost and sensor size reduction which are desirable.

In addition, by eliminating the number of requisite electrical contact points between the transmitter unit and the analyte sensor electrodes from three (working, reference and counter)

to two contact points (working and reference electrodes), analyte monitoring system failure can be improved, for example, resulting from introduction of foreign or undesirable matters such as water between the transmitter contacts and the respective electrodes of the analyte sensor.

In yet a further embodiment, the external counter electrode may be configured as a patient alert feature, such as an alarm for notifying failure modes of the sensor such as the adhesive failure. More specifically, by monitoring the signal level on the external counter electrode, alarm conditions may be easily and accurately provided to the patient. For example, displacement of the subcutaneously placed analyte sensor from the desired implanted position to a position where the measured values are no longer accurate can be detected by monitoring the voltage level of the external counter electrode. Moreover, in the case when the sensor is accidentally retracted from the implanted position, the counter electrode voltage will correspondingly change, and thus, such sensor failure mode may be easily and readily detected using the external counter electrode.

Accordingly, an analyte sensor system in one embodiment of the present invention includes a substrate, a first electrode disposed on a first surface of the substrate, a second electrode disposed on a second surface of the substrate, and a third electrode provided in electrical contact with at least one of the first or second electrode, where at least a portion of the first electrode and the second electrode are subcutaneously positioned in a patient, and where the third electrode is substantially entirely positioned external to the patient.

In one embodiment, the first electrode is a working electrode, the second electrode is a reference electrode, and the third electrode is a counter electrode.

Moreover, the first and second surfaces of the substrate may be the same. Alternatively, the first surface of the substrate may be on the opposite side of the substrate as the second surface of the substrate.

In still another embodiment, the analyte may include one of an interstitial fluid or blood.

The system in a further embodiment may include a second working electrode at least a portion of which is subcutaneously positioned in the patient.

The third electrode may in one embodiment include an external skin contact counter electrode.

In yet another embodiment, the system may also include a transmitter unit configured to establish electrical contact with one or more of the first, second or third electrodes.

Also, the third electrode maybe disposed on a surface of the transmitter unit such that at least a portion of the third electrode is in physical contact with the patient's skin and the transmitter unit.

Moreover, the system may additionally include an alarm unit configured to alert the patient when the third electrode physically separates from the skin of the patient. In one aspect, the alarm unit may be integrated in the transmitter unit.

A method of providing an analyte sensor in another embodiment includes providing a substrate, disposing a first electrode on a first surface of the substrate, disposing a second electrode on a second surface of the substrate, and positioning a third electrode in electrical contact with the first and second electrodes, where the third electrode is substantially entirely external to the patient.

The method may further include the step of disposing a second working electrode on either of said first or second surface of the substrate, where at least a portion of the second working electrode may be subcutaneously positioned in the patient.

A system for monitoring analyte in a patient in still a further embodiment of the present invention includes a sensor including a working electrode, a reference electrode, and a counter electrode, at least a portion of the sensor configured for transcutaneous placement in a patient such that the at least the portion of the sensor is in fluid contact with an analyte of the patient, and wherein the counter electrode is provided on the external surface of the patient's skin, and a transmitter unit operatively coupled to the sensor and configured to receive one or more signals from the sensor corresponding to an analyte level of the patient.

In one embodiment, the portion of the sensor in fluid contact with the patient's analyte includes a portion of the working electrode.

Additionally, the counter electrode may be positioned substantially completely external to the body of the patient, and further, the counter electrode may be configured for electrical communication with the transmitter unit.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An analyte sensor system, comprising:
    a substrate;
    a first electrode disposed on a first surface of the substrate;
    a second electrode disposed on a second surface of the substrate; and
    a transmitter unit configured for electrical communication with one or more of the first and second electrodes, and including a housing having a plurality of electrical contacts disposed thereon and configured for physical contact with a skin surface;
        wherein the plurality of electrical contacts are electrically coupled such that when the transmitter is positioned on the skin surface, one or more of the plurality of electrical contacts provide continuous electrical contact between the transmitter and the skin surface during a time period when at least a portion of the first electrode and the second electrodes are subcutaneously positioned under the skin surface.

2. The system of claim 1 wherein the first and second surfaces of the substrate are the same.

3. The system of claim 1 wherein the first surface of the substrate on the opposite side of the substrate as the second surface of the substrate.

4. The system of claim 1 wherein the analyte sensor includes a glucose sensor.

5. The system of claim 1 wherein the plurality of electrical contacts are coupled to a counter electrode contact of the transmitter unit.

6. The system of claim 1 wherein the plurality of electrical contacts are electrically coupled to each other such that when the transmitter unit is positioned on the skin surface, one or more of the plurality of electrical contacts provide continuous electrical contact between the skin surface and the transmitter unit.

7. The system of claim 1 wherein the time period includes one of approximately, three days, five days or seven days.

8. The system of claim 1 wherein the first electrode is a working electrode, and the second electrode is a reference electrode.

9. The system of claim 8 further including a second working electrode at least a portion of which is subcutaneously positionable in the patient.

10. The system of claim 1 further including an alarm unit, the alarm unit configured to alert the patient only when all of the plurality of the electrical contacts are no longer in physical contact with the skin surface at the same time.

11. The system of claim 10 wherein the alarm unit is integrated in the transmitter unit.

12. The system of claim 1 wherein the plurality of electrical contacts are disposed on the surface of the transmitter unit housing in a predetermined position.

13. The system of claim 12 wherein the predetermined position includes one or more of a concentric pattern or a circular pattern.

14. A method, comprising:
subcutaneously positioning at least a portion of an analyte sensor including a first electrode disposed on a first surface of a substrate and a second electrode disposed on a second surface of the substrate such that the portion of the analyte sensor is in fluid contact with an analyte under a skin surface; and
positioning a transmitter unit including a housing on the skin surface such that the transmitter unit is in electrical contact with the analyte sensor, the transmitter unit housing including a plurality of electrical contacts configured for contacting the skin surface, wherein at least one of the plurality of electrical contacts is in physical contact with the skin surface;
wherein the plurality of electrical contacts are electrically coupled and provide continuous electrical contact with the skin surface during a time period when the analyte sensor is in fluid contact with an interstitial fluid.

15. The method of claim 14 wherein the first and second surfaces of the substrate are the same.

16. The method of claim 14 wherein the first surface of the substrate on the opposite side of the substrate as the second surface of the substrate.

17. The method of claim 14 wherein the analyte sensor includes a glucose sensor.

18. The method of claim 14 including electrically coupling the plurality of electrical contacts to a counter electrode contact on the transmitter unit.

19. The method of claim 14 including coupling the plurality of electrical contacts to a common contact point such that when the transmitter is positioned on the skin surface, one or more of the plurality of electrical contacts provide continuous electrical contact between the skin surface and the transmitter unit.

20. The method of claim 14 wherein the first electrode is a working electrode and the second electrode is a reference electrode.

21. The method of claim 20 further including the step of disposing a second working electrode on either of said first or second surface of the substrate.

22. The method of claim 21 wherein at least a portion of the second working electrode is subcutaneously positioned under the skin surface.

23. The method of claim 14 wherein the plurality of electrical contacts are positioned on the surface of the transmitter housing in a predetermined pattern.

24. The method of claim 23 wherein the predetermined pattern includes one or more of a concentric pattern or a circular pattern.

* * * * *

UNITED STATES PATENT AND TRADEMARK OFFICE
CERTIFICATE OF CORRECTION

| | | |
|---|---|---|
| PATENT NO. | : 7,826,879 B2 | Page 1 of 1 |
| APPLICATION NO. | : 11/365169 | |
| DATED | : November 2, 2010 | |
| INVENTOR(S) | : Udo Hoss et al. | |

It is certified that error appears in the above-identified patent and that said Letters Patent is hereby corrected as shown below:

In the drawings, Sheet 1, Fig. 1, "Sensor Unit" in the box labeled 101 should be replaced with --Sensor--.

Specification
Column 1, line 8, replace "sensors" with --sensors,--.
Column 1, lines 8-9, replace "analyte sensor such as glucose sensors are" with --analyte sensor, such as a glucose sensor, is--.
Column 1, line 50, replace "is" with --are--.
Column 1, line 53, replace "sensor such as glucose sensors," with --sensor, such as a glucose sensor,--.
Column 3, line 18, replace "system 10" with --system 100--.
Column 4, line 17, replace "sensor unit 201" with --sensor 101--.
Column 4, line 22, replace "I the" with --in the--.
Column 6, line 9, replace "contact 603" with --contact 303--.
Column 6, line 57, replace "segment 420" with --segment 402--.
Column 6, line 58, replace "segment 410" with --segment 401--.
Column 8, line 12, replace "electrode 701" with --electrode 702--.
Column 8, line 13, replace "electrode 702" with --electrode 703--.
Column 8, line 34, replace "to electrically" with --to be electrically--.
Column 8, line 43, replace "housing 420" with --housing 410--.

Claims
Column 10, line 53, in claim 3, replace "substrate on" with --substrate is on--.
Column 12, line 7, in claim 16, replace "substrate on" with --substrate is on--.

Signed and Sealed this
Twenty-sixth Day of July, 2016

Michelle K. Lee
*Director of the United States Patent and Trademark Office*